United States Patent
Fujisato et al.

(10) Patent No.: US 7,883,864 B2
(45) Date of Patent: Feb. 8, 2011

(54) METHOD OF TREATING BIOLOGICAL TISSUE BY MICROWAVE-IRRADIATION

(75) Inventors: Toshiya Fujisato, Suita (JP); Akio Kishida, Suita (JP); Seiichi Funamoto, Suita (JP); Takeshi Nakatani, Suita (JP); Soichiro Kitamura, Suita (JP)

(73) Assignees: Japan as represented by President of National Cardiovascular Center, Osaka (JP); Nipro Corporation, Osaka (JP)

( * ) Notice: Subject to any disclaimer, the term of this patent is extended or adjusted under 35 U.S.C. 154(b) by 0 days.

(21) Appl. No.: 10/538,716

(22) PCT Filed: Dec. 11, 2003

(86) PCT No.: PCT/JP03/15914

§ 371 (c)(1),
(2), (4) Date: Jun. 10, 2005

(87) PCT Pub. No.: WO2004/052416

PCT Pub. Date: Jun. 24, 2004

(65) Prior Publication Data

US 2006/0115900 A1   Jun. 1, 2006

(30) Foreign Application Priority Data

Dec. 12, 2002 (JP) ............................. 2002-360094

(51) Int. Cl.
*G01N 1/30* (2006.01)
*G01N 33/48* (2006.01)
*A01N 1/00* (2006.01)
*A01N 1/02* (2006.01)

(52) U.S. Cl. .................. 435/40.5; 345/1.1; 424/572
(58) Field of Classification Search ............... 435/40.5, 435/1.1; 424/572
See application file for complete search history.

(56) References Cited

U.S. PATENT DOCUMENTS

| 4,963,708 | A  | * | 10/1990 | Kearns et al. ............... 219/731 |
| 4,994,237 | A  | * | 2/1991  | Login et al. .................. 435/1.1 |
| 5,571,216 | A  | * | 11/1996 | Anderson .................... 128/898 |
| 6,123,731 | A  | * | 9/2000  | Boyce et al. ............. 623/23.63 |
| 6,207,408 | B1 | * | 3/2001  | Essenfeld et al. .......... 435/40.5 |
| 6,875,583 | B2 | * | 4/2005  | Giberson et al. ........... 435/40.5 |

FOREIGN PATENT DOCUMENTS

| EP | 0362438 A1 | * | 4/1990 |
| JP | 04-288165  |   | 10/1992 |
| WO | WO 00/35374 |  | 6/2000 |

* cited by examiner

*Primary Examiner*—Thaian N Ton
(74) *Attorney, Agent, or Firm*—Millen, White, Zelano & Branigan, P.C.

(57) ABSTRACT

A method of efficiently removing or fixing donor cells from a native tissue of mammalian origin comprises immersing the tissue in a treating solution, and irradiating the tissue with microwave while maintaining the temperature thereof in the range between 0° C. and 40° C.

5 Claims, 3 Drawing Sheets

METHOD OF TREATING BIOLOGICAL TISSUE BY MICROWAVE-IRRADIATION

FIELD OF THE INVENTION

Figure 1:
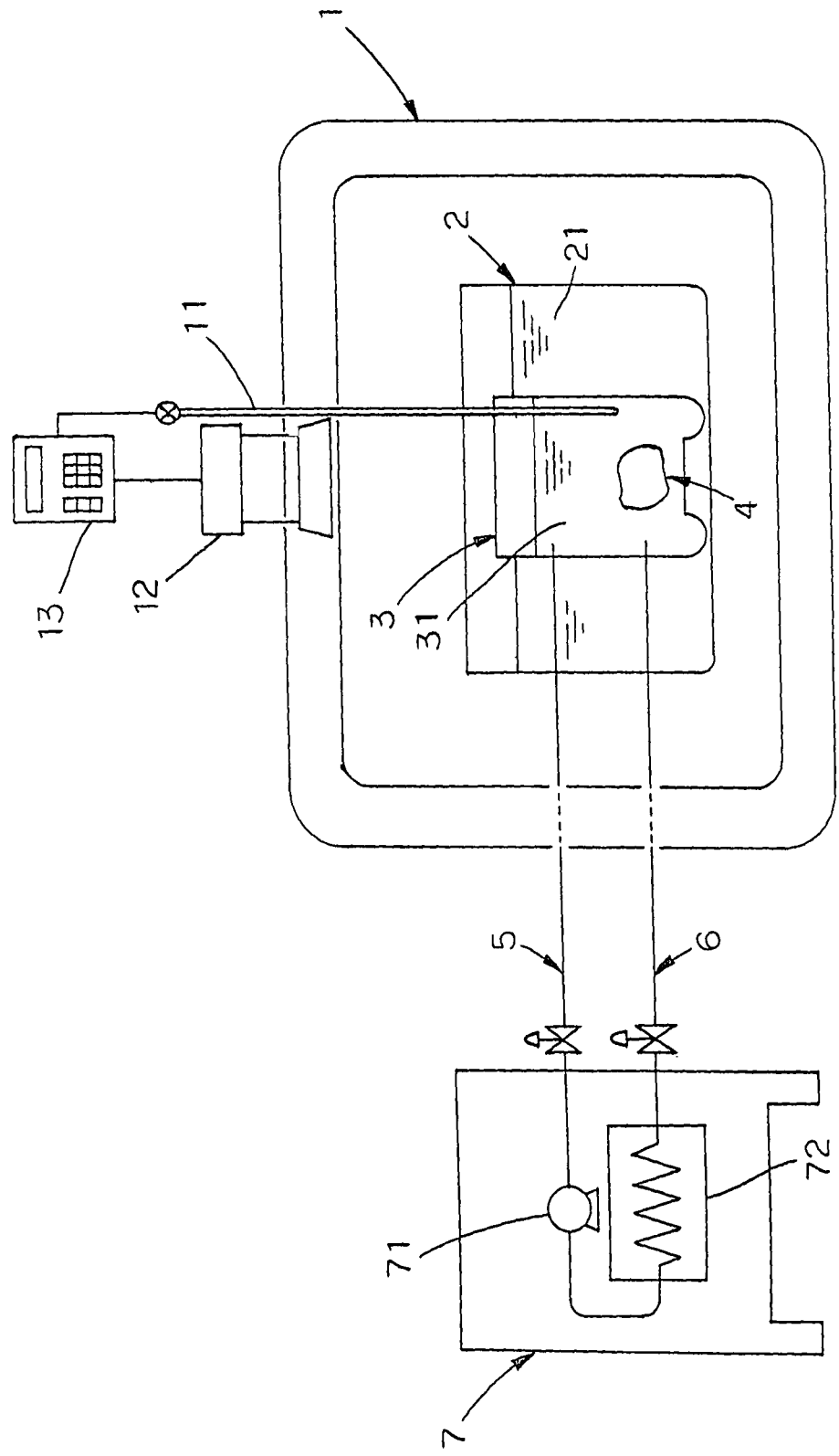

The present invention is in the field of regenerative medical technology in which the function of a particular organ or tissue of a patient is normalized by transplantation when the function is lost or otherwise abnormal. More particularly the invention relates to a method for preparing transplantable tissues from native tissues of mammalian origin by removing cell components or fixing the tissue using a fixing agent such as glutaraldehyde.

BACKGROUND ART

Scafold materials are prepared from native tissues for clinical application by chemically treating the tissue with a fixing agent such as glutaraldehyde or by decellularizing the tissue. In heart valve replacement, for example, xenogeneic heart valves are prepared from porcine heart valves or bovine pericardia by treatment with glutaraldehyde to diminish their immunogenicity. These xenogeneic valves are highly anti-clotting but durable only for 5-10 years in young recipients. Therefore, they are normally transplanted to older recipients over 60 years old.

Since tissue bank systems have been organized in Europe and America around 1985 and also in Japan in recent years, allogeneic cryopreserved valves from deceased donors have been clinically used. The allogeneic valves are less thrombogenic than mechanical valves, more durable than xenogeneic valves and less susceptible to infections than both. However, a critical problem is the fact that the number of available valves is absolutely insufficient. Moreover, cases in which functional failure appeared at a relatively early stage have been reported among young recipients suggesting the involvement of immune reactions. In the Ross operation know to be effective in young recipients, autologous pulmonary valve is transplanted to aortic valve site and the impaired pulmonary valve is reconstructed with cryopreserved allogeneic valve. The characteristic feature of the autologous pulmonary valve transplanted to the aortic valve site is that it is growable as the recipient grows. In contrast, mechanical valves and xenogeneic valves as well as cryopreserved allogeneic valves cannot grow and re-transplatation is often needed for children. In order to eliminate the above problems, several studies have been reported removing donor cells from allogeneic valves so that their immunogenicity and involvement of immune reactions are diminished to increase the durability and autogenesis of transplanted valves.

A decellularization method using a chemical solution called "SynerGraft" was developed by CryoLife, U.S.A. It was reported that the decellularized tissue by this method was infiltrated into autologous cellular structures within several months and recellularized with autologous cells.

Harverich et al. of Hannover University, School of Medicine, Germany published a decellularization method using the detergent Triton X-100 and proteolytic enzyme tripsin solutions.

However, washing with detergent or other chemical solutions alone is not sufficiently effective to remove bacteria, viruses and other contaminants from the interior of tissue because the washing depends on diffusion and penetration of the washing solution from surfaces of the tissue. Because of these limitations, complete decellularization and removal of bacteria and viruses are hardly possible for large tissue materials. In order to achieve satisfactory effects by chemical washing, it is necessary to increase the degree of treatment. This may lead to problems of post-graft calcification and removal of residual treating chemicals. As evidenced from BSE and CJD infections in transplantation, safety assurance is very important for the tissue to be transplanted. Currently known treating processes do not assure complete inactivation of viral contaminants and infection incidents may often occur from transplanted tissue contaminated with viruses.

The decellularized xenogeneic or allogeneic tissues are recellularized by seeding and culturing autologous cells for transplantation as a hybrid regenerative tissue.

DISCLOSURE OF THE INVENTION

It is, therefore, an object of this invention to provide a method which can eliminate or ameliorate the disadvantages of the prior art, namely, a method which can accomplish, first, removal of cellular components, bacteria and viruses from large size tissues, second, can enable treatment without impairing the biomechanical properties of the tissue, and, third, allows sterilization of the tissue in a simple manner in a short period of time.

The present invention, provides a method of treating native tissues of mammalian origin comprising immersing said tissue in a treating solution, and irradiating said tissue with microwaves while maintaining the temperature thereof at a temperature in the range between 0° C. and 40° C.

BRIEF DESCRIPTION OF THE ACCOMPANYING DRAWINGS

FIG. 1 is a schematic illustration of an exemplary system for carrying out the present invention.

Figure 2:
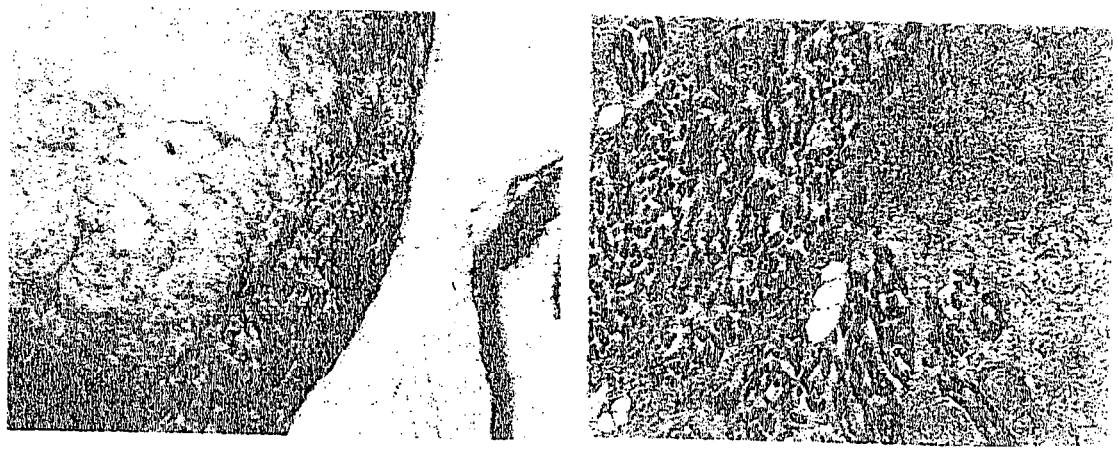

FIG. 2 is a microscopic view of a specimen of porcine heart valve tissue taken in cross-section. The specimen treated with the prior art solution is shown on the left while the specimen treated with the prior art solution in conjunction with microwave-irradiation according to the present invention is shown on the right. Residual nuclei are observed in the interior of the tissue treated with the prior art solution alone (lower left).

Figure 3:
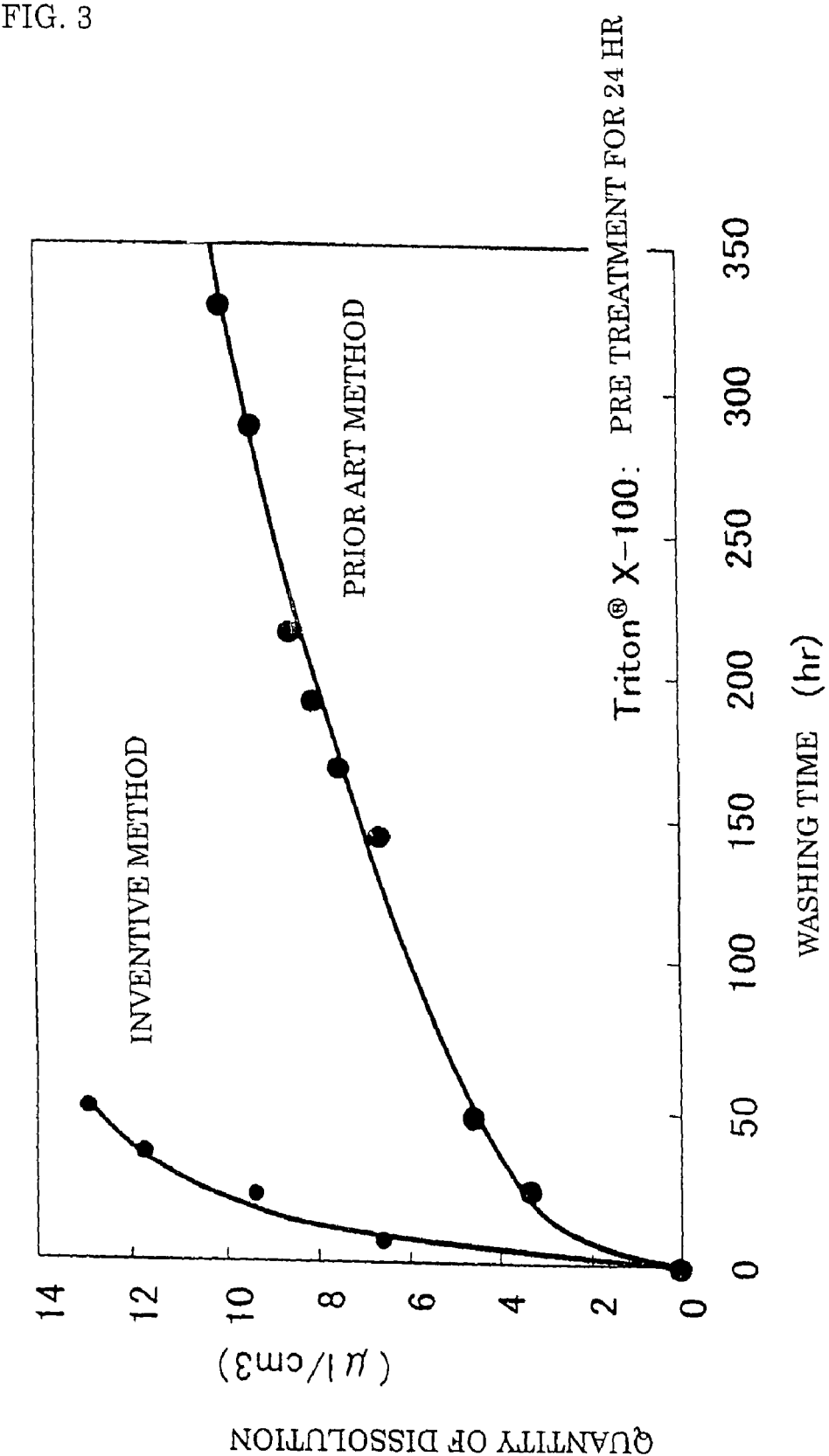

FIG. 3 is a graph showing the efficiency of removal of Triton X-100 from decellularized porcine heart valve. The method of the present invention enables the time required for removal of Triton X-100 to be decreased to about $\frac{1}{10}$ compared to the prior method.

BEST MODE FOR CARRYING OUT THE INVENTION

The method of the present invention involves treatment of native tissues to prepare transplantable tissues by decellularizing of the native tissues. In this case, the treating solution may be pure water, a hypertonic solution, a hypotonic solution, a detergent solution, an enzyme solution, a liquid medium, or a mixture thereof with a small proportion of an organic solvent.

The method of the present invention also involves preparing transplantable tissues by fixing native tissues. The treating solution in this case is a solution of fixing chemicals such as glutaraldehyde.

In either treatment, the prior art method without microwave-irradiation requires a relatively long period of time until the treating solution migrates throughout the tissue because the solution gradually diffuses and penetrates from the tissue surfaces. This may result in a risk of contamination of the tissue. The irradiation of native tissues with microwave in accordance with the present invention enables the treating time required for penetrating the treating solution throughout the tissue to be decreased to about 1/10 compared with the prior art method. Thus substantial improvement in the treatment efficiency may be achieved while preventing the tissue from contamination. Furthermore, the present invention can decellularize the tissue even from deep portions in a short period of time which has been otherwise difficult or impossible to accomplish.

Microwaves have hitherto been used in the field of histopathology e.g. for tissue fixing, bone decalcification, or defatting purposes, and in histoimmunological chemistry. It is believed, however, that the application of microwave for the purpose of preparation of transplantable tissues was not known.

In the new method according to the present invention, the native tissue of mammalian origin is placed in a container made of a microwave-transmitting material such as glass or a plastic. Then a treating solution is poured into the container until the tissue is completely immersed in the solution. The treating solution may be a detergent solution, a hypotonic solution or a hypertonic solution when decellularization is intended, or a solution of fixing chemicals such as glutaraldehyde when cell fixing is intended. The tissue in the treating solution is then irradiated with microwave while maintaining the tissue at a temperature between 0° C. and 40° C. Because the tissue is heated, it is necessary to cool the tissue during the irradiation with microwave. This may be accomplished using a commercially available rapid microwave-treatment apparatus by providing the apparatus with cooling means. To this end, the container containing the tissue and the treating solution is place in the microwave oven and a antifreezing coolant is circulated between the container and a cooling apparatus external of the microwave oven. A temperature sensor is disposed in the tissue container to control the microwave oven and the cooling apparatus in response to the sensed temperature to maintain the tissue at a temperature between 0° C. and 40° C. Apart from histopathological procedures, preparation of transplantable tissues requires preventing denaturing of tissue matrix so as to preserve the biomechanical properties thereof. Therefore, it is imperative to avoid temperature below 0° C. or above 40° C. during irradiation with microwaves.

An exemplary system for carrying out the present invention is shown schematically in FIG. 1. The system comprises a microwave oven 1 having a microwave generator 12. A coolant vessel 2 is disposed in the interior of the oven and filled with an anti-freezing coolant 21. The tissue container 3 containing a treating solution 31 and a tissue 4 to be treated is centrally placed in the coolant vessel 2. The coolant vessel 2 and the tissue container 3 are made of a microwave-transmitting material such a glass, polypropylene or polystyrene. As described earlier, the microwave will heat the treating solution 31 and thus the tissue 4 to irreversibly denature the tissue matrix by heat. Consequently, a cooling apparatus 7 is disposed externally to the oven 1 and the coolant 31 is circulated between the coolant vessel 2 and the cooling apparatus through the associated conduit means 5 and 6. The coolant 21 warmed in the vessel 2 is conveyed to a heat exchanger 72 of the cooling apparatus through the conduit 6 and the coolant cooled there is returned to the vessel 2 through the conduit 5 using a pump 71. The temperature of the coolant in the vessel 21 is monitored by a sensor 11 to generate a control signal. A controller 13 controls the operational time of the microwave generator 12 intermittently and automatically in response to the control signal to maintain the temperature at a constant level between 0° C. and 40° C., for example, at 10° C. Means for uniformly propagating the microwaves such as a fan or the like may be provided in the microwave oven.

The method of the present invention may be used in conjunction with a known decellularizing method. For example, the tissue may be pre-treated with a detergent solution or an enzyme solution to remove the cellular components and then irradiated with microwave to remove residual chemicals from the tissue by washing.

The method of the present invention finds use in the following treatments.

1. Soft Mammalian Tissues for Use in Transplantation

Decellularization of soft tissues obtained from donors with death due to cerebral or heart failure or xenogeneic porcine or bovine soft tissues for the preparation of transplantable tissues. The efficiency of removal of cellular components by washing in the subsequent step is largely improved. At the same time, the immunogenecity of the tissue is substantially diminished.

2. Hard Mammalian Tissues for Use in Transplantation

Similar to soft tissues, hard tissues such as bone, cartilage or teeth may be decellularized to prepare transplantable tissues.

3. Treatment of Other Biological Tissues for Medical Use

Tissues of animal or plant origin may be treated for the purpose of destructing cells therein.

EXAMPLES

1. Fresh porcine hearts were purchased from a breeding farm and transported at 4° C. The warm ischemic time of the heart was controlled within 20 minutes. Pulmonary valves and blood vessels were excised and washed with Hank's solution and immersed in a 1% solution of Triton X-100. Using the system schematically shown in FIG. 1, the excised tissues were irradiated with microwave intermittently at 20° C. to remove cells. After treating the tissue was washed with PBS to remove residual cells. Specimens of the decellularized tissue were stained with HE and histologically evaluated by the microscopic observation.

As shown in the photograph of FIG. 2, the porcine pulmonary valve leaflet was decellularized even in deep interior portions by the irradiation with microwave in conjunction with the treatment of the detergent solution while the treatment with the detergent solution alone failed to achieve decellularization.

2. Porcine heart valves purchased from the same breeding farm were decellularized by immersing in a 1% aqueous solution of Triton X-100 for 24 hours. Then the decellularized heart valves were immersed in PBS and irradiated with microwave intermittently at 10° C. for 48 hours. As shown in the graph of FIG. 3, cytotoxic Triton X-100 was removed from the tissue within several days by irradiation with microwaves while about 3 weeks were required to remove the detergent from the tissue when the tissue was not irradiated with microwaves.

The invention claimed is:

1. A method of decellularizing mammalian tissue comprising:
   a) immersing the mammalian tissue in a treatment solution comprising a detergent but lacking of a fixation chemical;
   b) irradiating said tissue with microwaves at a frequency of 2451 MHz for a net period of at least 1 hour while maintaining the temperature of the tissue in a range between 0° C. and 40° C.;

c) washing the irradiated tissue to remove residual cells, leaving a washed tissue;

whereby the tissue is decellularized even in deep interior portions if determined by:

d) staining a specimen from the washed tissue from c) with hematoxylin-eosin stain and histologically evaluating the specimen by microscopic observation to determine any residual cellular nuclei;

e) identifying the tissue as decellularized when the specimen is marked by absence of any residual cellular nuclei even in deep interior portions.

2. The method of claim 1 wherein said native tissue to be treated is soft tissue including vascular vessel, heart valve, heart sac, cornea, amonion and dura.

3. The method of claim 1 wherein said native tissue to be treated is an organ or part thereof including heart, kidney, liver, pancreas, brain and part thereof.

4. The method of claim 1 wherein said native tissue to be treated has been pre-treated to facilitate the removal of donor cells.

5. The method of claim 1 wherein said tissue is immersed in said treating solution received in a microwave-transmitting container which, is, in turn, in heat-exchange contact with a coolant liquid received in a microwave-transmitting vessel, and wherein said tissue is irradiated with microwaves in a microwave oven while circulating said coolant liquid through a cooling apparatus provided externally of the microwave oven.

* * * * *